United States Patent
Pfister et al.

(10) Patent No.: US 10,913,787 B2
(45) Date of Patent: Feb. 9, 2021

(54) METHOD OF IDENTIFYING MUSK COMPOUNDS

(71) Applicant: Firmenich SA, Geneva (CH)

(72) Inventors: Patrick Pfister, Brooklyn, NY (US); Matthew Rogers, Briarcliff Manor, NY (US)

(73) Assignee: Firmenich SA, Satigny (CH)

( * ) Notice: Subject to any disclaimer, the term of this patent is extended or adjusted under 35 U.S.C. 154(b) by 350 days.

(21) Appl. No.: 15/580,476

(22) PCT Filed: Jun. 9, 2016

(86) PCT No.: PCT/US2016/036776
§ 371 (c)(1),
(2) Date: Dec. 7, 2017

(87) PCT Pub. No.: WO2016/201152
PCT Pub. Date: Dec. 15, 2016

(65) Prior Publication Data
US 2020/0048326 A1     Feb. 13, 2020

Related U.S. Application Data

(60) Provisional application No. 62/173,762, filed on Jun. 10, 2015.

(51) Int. Cl.
*C07K 14/72*     (2006.01)
*G01N 33/50*     (2006.01)

(52) U.S. Cl.
CPC ....... *C07K 14/723* (2013.01); *G01N 33/5008* (2013.01); *G01N 2333/726* (2013.01)

(58) Field of Classification Search
None
See application file for complete search history.

(56) References Cited

U.S. PATENT DOCUMENTS

| 6,852,244 B2* | 2/2005 | Egawa | D06M 13/184 252/8.61 |
| 2009/0081701 A1* | 3/2009 | Cen | G01N 33/554 435/7.2 |
| 2010/0248390 A1 | 9/2010 | Matsunami et al. | |

FOREIGN PATENT DOCUMENTS

| EP | 0283234 A2 | 9/1988 |
| EP | 2832347 A1 | 2/2015 |
| WO | 200127158 A2 | 4/2001 |
| WO | 2002018657 A1 | 3/2002 |
| WO | 2014210585 A2 | 12/2014 |
| WO | 2015020158 A1 | 2/2015 |

OTHER PUBLICATIONS

International Search report and Written Opinion for application No. PCT/US2016/036776, dated Aug. 17, 2016.
Shirasu et al., "Olfactory receptor and neural pathway responsible for highly selective sensing of musk odors," Neuron Cell Press, vol. 81, No. 1, p. 165-178, 2013.
Malnic et al., "Combinatorial receptor codes for odors," Cell Press, vol. 96, p. 713-723, 1999.
Marko et al., "A robust method for the amplification of RNA in the sense orientation," BMC Genomics, BioMed Central, vol. 6, No. 27, p. 1-13, 2005.
Metzker, M., "Sequencing technologies—the next generation," Nature Reviews/ Genetics, vol. 11, p. 31-46, 2010.
Adipietro et al., "Functional evolution of mammalian odorant receptors," PLOS Genetics, vol. 8, No. 7, p. 1-14, 2012.
Kyte et al., "A simple method for displaying the hydropathic character of a protein," J. Mol. Biol., vol. 157, p. 105-132, 1982.
"Sequence 1344 from Patent WO0127158," EBI accession No. AX242596, 2001, 1 page.
"Sequence 1888 from Patent WO0127158," EBI accession No. AX243140, 2001, 1 page.
"Sequence 2381 from Patent WO0127158," EBI accession No. AX243633, 2001, 1 page.
"Murine OR-like polypeptide query sequence, SEQ ID No. 2382," EBI accession No. AAG72700, 2001, 1 page.
"Odorant receptor identification related protein, SEQ ID 1119," EBI accession No. AYJ85275, 2010, 1 page.
"Odorant receptor identification related protein, SEQ ID 1118," EBI accession No. AYJ85274, 2010, 1 page.
"Sequence 2 from Patent EP2832347," EBI accession No. JD592755, 2015.
"Human olfactory receptor family 11 subfamily A member 1 protein, SEQ 2," EBI accession No. BBU46526, 2015, 1 page.
"Human OR11A1 protein sequence," EBI accession No. AAU79199, 2007, 2 pages.
Araneda, R., et al., "A pharmacological profile of the aldehyde receptor repertoire in rat olfactory epithelium." J. Physiol, vol. 555, No. 3, p. 743-756, 2004.

* cited by examiner

*Primary Examiner* — John D Ulm
(74) *Attorney, Agent, or Firm* — Paul Zagar

(57) ABSTRACT

Provided herein are polypeptides that bind to Musk compounds. Also provided are nucleic acid sequences that encode for the polypeptides. Further provided herein is a method for identifying a compound that activates, mimics, blocks, inhibits, modulates, and/or enhances the activity of an olfactory receptor that is activated by a polycyclic Musk or a nitro Musk wherein the receptor is a polypeptide having an amino acid sequence that is at least 75% identical to Olfr96 or OR11A1, wherein the method includes a) contacting the receptor, or a chimera or fragment thereof with a compound and b) determining whether the compound has an effect on the activity of the receptor.

2 Claims, 2 Drawing Sheets
Specification includes a Sequence Listing.

SEQUENCE LISTING

```
<160> NUMBER OF SEQ ID NOS: 10

<210> SEQ ID NO 1
<211> LENGTH: 942
<212> TYPE: DNA
<213> ORGANISM: mouse

<400> SEQUENCE: 1
atgggaatcc tttccacagg aaatcaaact gtcactgagt ttgtacttct tggtttccat    60
gaagtccctg ggctgcacct cctgtttttt tctgtgttca ccatcctcta tgcctccatc   120
atcacaggga acatgctcat tgcagtggtg gtggtgagct cccagaggct tcacacaccc   180
atgtatttct ttctggtgaa tctgtccttc atagagattg tctataccctc cacagtggtg   240 cccaaaatgc tggaaggctt cttacaggag gccaccatat ctgtggctgg ctgcttgctc   300
```

| | | |
|---|---|---|
| cagttctttg tttttggctc tctggccaca gatgagtgtt ttctgctggc tgtgatggca | 360 | |
| tatgatcgat atctcgcaat ttgtcaccct ctacgatacc cacacctcat ggggcctcaa | 420 | |
| tggtgcctgg ggttggtgct cacagtctgg ctgtctggct tcatggtaga tggactagtt | 480 | |
| gttgctctga tgcccagttg agattctgtg gccccaactt agttgatcac tttttactgt | 540 | |
| gattttttcac ctttgatggt cctggcttgc tcagataccc aagtggccca ggtgactaca | 600 | |
| tttgttctct ctgtggtctt cctgactgtc ccctttgggc tggttctgat ctcctatgct | 660 | |
| cagattgtag tgactgtgct gagagttcct tctgggacca aagaaccaa ggccttctcc | 720 | |
| acatgctcct ctcacctggc tgtggtgtcc acgttctatg aacactcat ggtattgtac | 780 | |
| attgtgccct ctgctgttca ttctcagctc ctctccaagg tcattgccct gctctacaca | 840 | |
| gtggtcactc ccatcttcaa ccctgtcatc tacaccttga ggaaccagga ggtgcagcag | 900 | |
| gcactaagaa ggcttctcta ctgcaaacca actgaaatgt ga | 942 | |

<210> SEQ ID NO 2
<211> LENGTH: 313
<212> TYPE: PRT
<213> ORGANISM: mouse

<400> SEQUENCE: 2

Met Gly Ile Leu Ser Thr Gly Asn Gln Thr Val Thr Glu Phe Val Leu
1               5                   10                  15

Leu Gly Phe His Glu Val Pro Gly Leu His Leu Phe Phe Ser Val
            20                  25                  30

Phe Thr Ile Leu Tyr Ala Ser Ile Ile Thr Gly Asn Met Leu Ile Ala
        35                  40                  45

Val Val Val Ser Ser Gln Arg Leu His Thr Pro Met Tyr Phe Phe
    50                  55                  60

Leu Val Asn Leu Ser Phe Ile Glu Ile Val Tyr Thr Ser Thr Val Val
65                  70                  75                  80

Pro Lys Met Leu Glu Gly Phe Leu Gln Glu Ala Thr Ile Ser Val Ala
                85                  90                  95

Gly Cys Leu Leu Gln Phe Phe Val Phe Gly Ser Leu Ala Thr Asp Glu
            100                 105                 110

Cys Phe Leu Leu Ala Val Met Ala Tyr Asp Arg Tyr Leu Ala Ile Cys
        115                 120                 125

His Pro Leu Arg Tyr Pro His Leu Met Gly Pro Gln Trp Cys Leu Gly
    130                 135                 140

Leu Val Leu Thr Val Trp Leu Ser Gly Phe Met Val Asp Gly Leu Val
145                 150                 155                 160

Val Ala Leu Met Ala Gln Leu Arg Phe Cys Gly Pro Asn Leu Val Asp
                165                 170                 175

His Phe Tyr Cys Asp Phe Ser Pro Leu Met Val Leu Ala Cys Ser Asp
            180                 185                 190

Thr Gln Val Ala Gln Val Thr Thr Phe Val Leu Ser Val Val Phe Leu
        195                 200                 205

Thr Val Pro Phe Gly Leu Val Leu Ile Ser Tyr Ala Gln Ile Val Val
    210                 215                 220

Thr Val Leu Arg Val Pro Ser Gly Thr Arg Arg Thr Lys Ala Phe Ser
225                 230                 235                 240

Thr Cys Ser Ser His Leu Ala Val Val Ser Thr Phe Tyr Gly Thr Leu
                245                 250                 255

Met Val Leu Tyr Ile Val Pro Ser Ala Val His Ser Gln Leu Leu Ser

```
            260                 265                 270
Lys Val Ile Ala Leu Leu Tyr Thr Val Val Thr Pro Ile Phe Asn Pro
            275                 280                 285

Val Ile Tyr Thr Leu Arg Asn Gln Glu Val Gln Gln Ala Leu Arg Arg
            290                 295                 300

Leu Leu Tyr Cys Lys Pro Thr Glu Met
305                 310
```

```
<210> SEQ ID NO 3
<211> LENGTH: 948
<212> TYPE: DNA
<213> ORGANISM: human

<400> SEQUENCE: 3
```

| | | | | | |
|---|---|---|---|---|---|
| atggaaattg | tctccacagg | aaacgaaact | attactgaat | tgtcctcct | tggcttctat | 60 |
| gacatccctg | aactgcattt | cttgtttttt | attgtattca | ctgctgtcta | tgtcttcatc | 120 |
| atcatagggca | atatgctgat | tattgtagca | gtggttagct | cccagaggct | ccacaaaccc | 180 |
| atgtatattt | tcttggcgaa | tctgtccttc | ctggatattc | tctacacctc | cgcagtgatg | 240 |
| ccaaaaatgc | tggagggctt | cctgcaagaa | gcaactatct | ctgtggctgg | ttgcttgctc | 300 |
| cagttctta | tcttcggctc | tctagccaca | gctgaatgct | tactgctggc | tgtcatggca | 360 |
| tatgaccgct | acctggcaat | tgctaccca | ctccactacc | cactcctgat | ggggcccaga | 420 |
| cggtacatgg | ggctggtggt | cacaacctgg | ctctctggat | tgtggtagaa | tggactggtt | 480 |
| gtggccctgg | tggcccagct | gaggttctgt | ggccccaacc | acattgacca | gttttactgt | 540 |
| gactttatgc | ttttcgtggg | cctggcttgc | tcggatccca | gagtggctca | ggtgacaact | 600 |
| ctcattctgt | ctgtgttctg | cctcactatt | cctttggac | tgattctgac | atcttatgcc | 660 |
| agaattgtgg | tggcagtgct | gagagttcct | gctggggcaa | gcaggagaag | ggcttttctcc | 720 |
| acatgctcct | cccacctagc | tgtagtgacc | acattctatg | aacgctcat | gatctttat | 780 |
| gttgcaccct | ctgctgtcca | ttcccagctc | ctctccaagg | tcttctccct | gctctacact | 840 |
| gtggtcaccc | ctctcttcaa | tcctgtgatc | tataccatga | ggaacaagga | ggtgcatcag | 900 |
| gcacttcgga | agattctctg | tatcaaacaa | actgaaacac | ttgattga | | 948 |

```
<210> SEQ ID NO 4
<211> LENGTH: 315
<212> TYPE: PRT
<213> ORGANISM: human

<400> SEQUENCE: 4
```

```
Met Glu Ile Val Ser Thr Gly Asn Glu Thr Ile Thr Glu Phe Val Leu
1               5                   10                  15

Leu Gly Phe Tyr Asp Ile Pro Glu Leu His Phe Leu Phe Ile Val
                20                  25                  30

Phe Thr Ala Val Tyr Val Phe Ile Ile Gly Asn Met Leu Ile Ile
            35                  40                  45

Val Ala Val Val Ser Ser Gln Arg Leu His Lys Pro Met Tyr Ile Phe
        50                  55                  60

Leu Ala Asn Leu Ser Phe Leu Asp Ile Leu Tyr Thr Ser Ala Val Met
65                  70                  75                  80

Pro Lys Met Leu Glu Gly Phe Leu Gln Glu Ala Thr Ile Ser Val Ala
                85                  90                  95

Gly Cys Leu Leu Gln Phe Ile Phe Gly Ser Leu Ala Thr Ala Glu
            100                 105                 110
```

```
Cys Leu Leu Leu Ala Val Met Ala Tyr Asp Arg Tyr Leu Ala Ile Cys
        115                 120                 125

Tyr Pro Leu His Tyr Pro Leu Leu Met Gly Pro Arg Arg Tyr Met Gly
    130                 135                 140

Leu Val Val Thr Thr Trp Leu Ser Gly Phe Val Val Asp Gly Leu Val
145                 150                 155                 160

Val Ala Leu Val Ala Gln Leu Arg Phe Cys Gly Pro Asn His Ile Asp
                165                 170                 175

Gln Phe Tyr Cys Asp Phe Met Leu Phe Val Gly Leu Ala Cys Ser Asp
            180                 185                 190

Pro Arg Val Ala Gln Val Thr Thr Leu Ile Leu Ser Val Phe Cys Leu
        195                 200                 205

Thr Ile Pro Phe Gly Leu Ile Leu Thr Ser Tyr Ala Arg Ile Val Val
    210                 215                 220

Ala Val Leu Arg Val Pro Ala Gly Ala Ser Arg Arg Arg Ala Phe Ser
225                 230                 235                 240

Thr Cys Ser Ser His Leu Ala Val Val Thr Thr Phe Tyr Gly Thr Leu
                245                 250                 255

Met Ile Phe Tyr Val Ala Pro Ser Ala Val His Ser Gln Leu Leu Ser
            260                 265                 270

Lys Val Phe Ser Leu Leu Tyr Thr Val Thr Pro Leu Phe Asn Pro
        275                 280                 285

Val Ile Tyr Thr Met Arg Asn Lys Glu Val His Gln Ala Leu Arg Lys
    290                 295                 300

Ile Leu Cys Ile Lys Gln Thr Glu Thr Leu Asp
305                 310                 315

<210> SEQ ID NO 5
<211> LENGTH: 24
<212> TYPE: DNA
<213> ORGANISM: artificial
<220> FEATURE:
<223> OTHER INFORMATION: Flag tag

<400> SEQUENCE: 5
gattacaagg acgacgacga taag                                          24

<210> SEQ ID NO 6
<211> LENGTH: 8
<212> TYPE: PRT
<213> ORGANISM: artificial
<220> FEATURE:
<223> OTHER INFORMATION: Flag tag

<400> SEQUENCE: 6

Asp Tyr Lys Asp Asp Asp Asp Lys
1               5

<210> SEQ ID NO 7
<211> LENGTH: 60
<212> TYPE: DNA
<213> ORGANISM: artificial
<220> FEATURE:
<223> OTHER INFORMATION: Rho tag

<400> SEQUENCE: 7
atgaacggga ccgagggccc aaacttctac gtgcctttct ccaacaagac gggcgtggtg   60

<210> SEQ ID NO 8
```

-continued

```
<211> LENGTH: 20
<212> TYPE: PRT
<213> ORGANISM: artificial
<220> FEATURE:
<223> OTHER INFORMATION: Rho tag

<400> SEQUENCE: 8

Met Asn Gly Thr Glu Gly Pro Asn Phe Tyr Val Pro Phe Ser Asn Lys
1               5                   10                  15

Thr Gly Val Val
            20

<210> SEQ ID NO 9
<211> LENGTH: 51
<212> TYPE: DNA
<213> ORGANISM: artificial
<220> FEATURE:
<223> OTHER INFORMATION: Lucy tag

<400> SEQUENCE: 9
atgagacccc agatcctgct gctcctggcc ctgctgaccc taggcctggc t         51

<210> SEQ ID NO 10
<211> LENGTH: 17
<212> TYPE: PRT
<213> ORGANISM: artificial
<220> FEATURE:
<223> OTHER INFORMATION: Lucy tag

<400> SEQUENCE: 10

Met Arg Pro Gln Ile Leu Leu Leu Ala Leu Leu Thr Leu Gly Leu
1               5                   10                  15

Ala
```

METHOD OF IDENTIFYING MUSK COMPOUNDS

FIELD

The technical field is directed to odorant and aroma receptors and assays that can be used to identify odorant and/or aroma compounds and more specifically enhancers of Musk compounds.

BACKGROUND

Olfaction is one of the most complex and poorly understood of human sensory systems. From olfactory receptor (OR) activation to perception, there are many steps that still require further investigation. Musk compounds are part of a structurally diverse group of chemicals comprising macrocyclic Musks, polycyclic Musks, alicyclic Musks and nitro Musks. These Musk compounds are used in perfumery, and form the base notes in many commercial formulations. Hence, there is a need to identify new Musk compounds and compounds that enhance the perception of Musk in perfumes.

SUMMARY

Provided herein is a host cell transformed to express a polypeptide having an amino acid sequence that is at least 75% identical to SEQ ID NO: 2 or SEQ ID NO: 4.

Further provided herein is an expression vector comprising a nucleic acid that encodes for a polypeptide having an amino acid sequence that is at least 75% identical to SEQ ID NO: 2 or SEQ ID NO: 4.

Also provided herein is an expression vector having a nucleic acid wherein the nucleic acid comprises a nucleotide sequence that is at least 75% identical to SEQ ID NO: 1 or SEQ ID NO: 3.

Further provided herein is a method for identifying a compound that blocks, inhibits, modulates, and/or enhances the activity of an olfactory receptor that is activated by a polycyclic musk or a nitro musk wherein the receptor is a polypeptide having an amino acid sequence that is at least 75% identical to SEQ ID NO: 2 or SEQ ID NO: 4 wherein the method comprises:
  a) contacting the receptor, or a chimera or fragment thereof with a compound;
  b) determining whether the compound has an effect on the activity of the receptor.

Still yet further provided is a cell that is recombinantly modified to express a polypeptide described above.

DETAILED DESCRIPTION OF THE DRAWINGS

FIG. 1 displays $Ca^{2+}$ imaging traces of olfactory sensory neurons that responded to mixtures of musk compounds (FIG. 1A) and the subsequent identification of mouse receptors Olfr96 and Olfr235 (FIG. 1 B).

DETAILED DESCRIPTION

Figure 1:
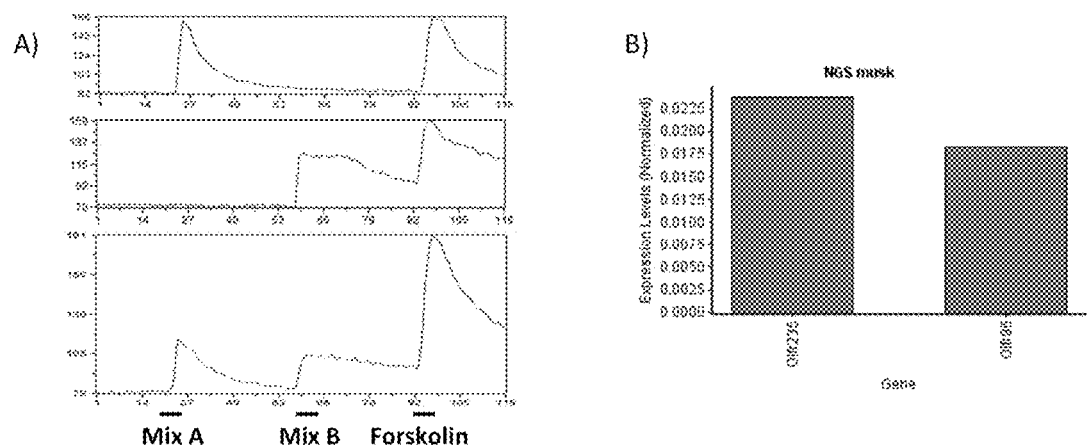

For the descriptions herein and the appended claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

In one embodiment, a host cell is transformed to express a polypeptide wherein the polypeptide comprises an amino acid sequence is at least 75%, 80%, 85%, 90%, 95%, 98% or 99% identical to SEQ ID NO: 2.

In one embodiment, a host cell is transformed to express a polypeptide wherein the polypeptide comprises an amino acid sequence is at least 80%, 85%, 90%, 95%, 98% or 99% identical to SEQ ID NO: 2.

In one embodiment, a host cell is transformed to express a polypeptide wherein the polypeptide comprises an amino acid sequence is at least 85%, 90%, 95%, 98% or 99% identical to SEQ ID NO: 2.

In one embodiment, a host cell is transformed to express a polypeptide wherein the polypeptide comprises an amino acid sequence is at least 90%, 95%, 98% or 99% identical to SEQ ID NO: 2.

In one embodiment, a host cell is transformed to express a polypeptide wherein the polypeptide comprises an amino acid sequence is at least 95%, 98% or 99% identical to SEQ ID NO: 2.

In one embodiment, a host cell is transformed to express a polypeptide wherein the polypeptide comprises an amino acid sequence is at least 98% or 99% identical to SEQ ID NO: 2.

In one embodiment, a host cell is transformed to express a polypeptide wherein the polypeptide comprises an amino acid sequence is at least 99% identical to SEQ ID NO: 2.

In one embodiment, a host cell is transformed to express a polypeptide wherein the polypeptide comprises an amino acid sequence is at least 75%, 80%, 85%, 90%, 95%, 98% or 99% identical to SEQ ID NO: 4.

In one embodiment, a host cell is transformed to express a polypeptide wherein the polypeptide comprises an amino acid sequence is at least 80%, 85%, 90%, 95%, 98% or 99% identical to SEQ ID NO: 4.

In one embodiment, a host cell is transformed to express a polypeptide wherein the polypeptide comprises an amino acid sequence is at least 85%, 90%, 95%, 98% or 99% identical to SEQ ID NO: 4.

In one embodiment, a host cell is transformed to express a polypeptide wherein the polypeptide comprises an amino acid sequence is at least 90%, 95%, 98% or 99% identical to SEQ ID NO: 4.

In one embodiment, a host cell is transformed to express a polypeptide wherein the polypeptide comprises an amino acid sequence is at least 95%, 98% or 99% identical to SEQ ID NO: 4.

In one embodiment, a host cell is transformed to express a polypeptide wherein the polypeptide comprises an amino acid sequence is at least 98% or 99% identical to SEQ ID NO: 4.

In one embodiment, a host cell is transformed to express a polypeptide wherein the polypeptide comprises an amino acid sequence is at least 99% identical to SEQ ID NO: 4.

In one embodiment, a host cell is transformed to express a having an amino acid sequence that is identical to SEQ ID NO: 2 or SEQ ID NO: 4; more particularly an amino acid sequence that is identical to SEQ ID NO: 2; even more particularly an amino acid sequence that is identical to SEQ ID NO.: 4.

Further provided herein is an expression vector comprising a nucleic acid that encodes for a polypeptide having an amino acid sequence that is at least 75%, 80%, 85%, 90%, 95%, 98% or 99% identical to SEQ ID NO: 2.

Further provided herein is an expression vector comprising a nucleic acid that encodes for a polypeptide having an amino acid sequence that is at least 80%, 85%, 90%, 95%, 98% or 99% identical to SEQ ID NO: 2.

Further provided herein is an expression vector comprising a nucleic acid that encodes for a polypeptide having an amino acid sequence that is at least 85%, 90%, 95%, 98% or 99% identical to SEQ ID NO: 2.

Further provided herein is an expression vector comprising a nucleic acid that encodes for a polypeptide having an amino acid sequence that is at least 90%, 95%, 98% or 99% identical to SEQ ID NO: 2.

Further provided herein is an expression vector comprising a nucleic acid that encodes for a polypeptide having an amino acid sequence that is at least 95%, 98% or 99% identical to SEQ ID NO: 2.

Further provided herein is an expression vector comprising a nucleic acid that encodes for a polypeptide having an amino acid sequence that is at least 98% or 99% identical to SEQ ID NO: 2.

Further provided herein is an expression vector comprising a nucleic acid that encodes for a polypeptide having an amino acid sequence that is at least 99% identical to SEQ ID NO: 2.

Further provided herein is an expression vector comprising a nucleic acid that encodes for a polypeptide having an amino acid sequence that is at least 75%, 80%, 85%, 90%, 95%, 98% or 99% identical to SEQ ID NO: 4.

Further provided herein is an expression vector comprising a nucleic acid that encodes for a polypeptide having an amino acid sequence that is at least 80%, 85%, 90%, 95%, 98% or 99% identical to SEQ ID NO: 4.

Further provided herein is an expression vector comprising a nucleic acid that encodes for a polypeptide having an amino acid sequence that is at least 85%, 90%, 95%, 98% or 99% identical to SEQ ID NO: 4.

Further provided herein is an expression vector comprising a nucleic acid that encodes for a polypeptide having an amino acid sequence that is at least 90%, 95%, 98% or 99% identical to SEQ ID NO: 4.

Further provided herein is an expression vector comprising a nucleic acid that encodes for a polypeptide having an amino acid sequence that is at least 95%, 98% or 99% identical to SEQ ID NO: 4.

Further provided herein is an expression vector comprising a nucleic acid that encodes for a polypeptide having an amino acid sequence that is at least 98% or 99% identical to SEQ ID NO: 4.

Further provided herein is an expression vector comprising a nucleic acid that encodes for a polypeptide having an amino acid sequence that is at least 99% identical to SEQ ID NO: 4.

Further provided herein is an expression vector comprising a nucleic acid that encodes for a polypeptide having an amino acid sequence that is identical to SEQ ID NO: 2 or SEQ ID NO: 4; more particularly an amino acid sequence that is identical to SEQ ID NO: 2; even more particularly an amino acid sequence that is identical to SEQ ID NO: 4.

Also provided herein is an expression vector having a nucleic acid wherein the nucleic acid comprises a nucleotide sequence that is at least 75%, 80%, 85%, 90%, 95%, 98% or 99% identical to SEQ ID NO: 1.

Also provided herein is an expression vector having a nucleic acid wherein the nucleic acid comprises a nucleotide sequence that is at least 80%, 85%, 90%, 95%, 98% or 99% identical to SEQ ID NO: 1.

Also provided herein is an expression vector having a nucleic acid wherein the nucleic acid comprises a nucleotide sequence that is at least 85%, 90%, 95%, 98% or 99% identical to SEQ ID NO: 1.

Also provided herein is an expression vector having a nucleic acid wherein the nucleic acid comprises a nucleotide sequence that is at least 90%, 95%, 98% or 99% identical to SEQ ID NO: 1.

Also provided herein is an expression vector having a nucleic acid wherein the nucleic acid comprises a nucleotide sequence that is at least 95%, 98% or 99% identical to SEQ ID NO: 1.

Also provided herein is an expression vector having a nucleic acid wherein the nucleic acid comprises a nucleotide sequence that is at least 98% or 99% identical to SEQ ID NO: 1.

Also provided herein is an expression vector having a nucleic acid wherein the nucleic acid comprises a nucleotide sequence that is at least 99% identical to SEQ ID NO: 1.

Also provided herein is an expression vector having a nucleic acid wherein the nucleic acid comprises a nucleotide sequence that is at least 75%, 80%, 85%, 90%, 95%, 98% or 99% identical to SEQ ID NO: 3.

Also provided herein is an expression vector having a nucleic acid wherein the nucleic acid comprises a nucleotide sequence that is at least 80%, 85%, 90%, 95%, 98% or 99% identical to SEQ ID NO: 3.

Also provided herein is an expression vector having a nucleic acid wherein the nucleic acid comprises a nucleotide sequence that is at least 85%, 90%, 95%, 98% or 99% identical to SEQ ID NO: 3.

Also provided herein is an expression vector having a nucleic acid wherein the nucleic acid comprises a nucleotide sequence that is at least 90%, 95%, 98% or 99% identical to SEQ ID NO: 3.

Also provided herein is an expression vector having a nucleic acid wherein the nucleic acid comprises a nucleotide sequence that is at least 95%, 98% or 99% identical to SEQ ID NO: 3.

Also provided herein is an expression vector having a nucleic acid wherein the nucleic acid comprises a nucleotide sequence that is at least 98% or 99% identical to SEQ ID NO: 3. Also provided herein is an expression vector having a nucleic acid wherein the nucleic acid comprises a nucleotide sequence that is at least 99% identical to SEQ ID NO: 3.

Also provided herein is an expression vector having a nucleic acid wherein the nucleic acid comprises a nucleotide sequence that is identical to SEQ ID NO: 1.

Also provided herein is an expression vector having a nucleic acid wherein the nucleic acid comprises a nucleotide sequence that is identical to SEQ ID NO: 3.

In one embodiment provided herein is a cell that is recombinantly modified to express a polypeptide having an amino acid sequence that is at least 75% identical to SEQ ID NO: 2 or SEQ ID NO: 4.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 75% identical to SEQ ID NO: 2 or SEQ ID NO: 4 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 75%, 80%, 85%, 90%, 95%, 98% and 99% identical to SEQ ID NO: 2 wherein the method comprises:
 c) contacting the receptor, or a chimera or fragment thereof with a compound;
 d) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 80%, 85%, 90%, 95%, 98% and 99% identical to SEQ ID NO: 2 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 85%, 90%, 95%, 98% and 99% identical to SEQ ID NO: 2 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 90%, 95%, 98% and 99% identical to SEQ ID NO: 2 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 95%, 98% and 99% identical to SEQ ID NO: 2 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 98% and 99% identical to SEQ ID NO: 2 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 99% identical to SEQ ID NO: 2 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 75%, 80%, 85%, 90%, 95%, 98% and 99% identical to SEQ ID NO: 4 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 80%, 85%, 90%, 95%, 98% and 99% identical to SEQ ID NO: 4 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 85%, 90%, 95%, 98% and 99% identical to SEQ ID NO: 4 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 90%, 95%, 98% and 99% identical to SEQ ID NO: 4 wherein the method comprises:
 a) contacting the receptor, or a chimera or fragment thereof with a compound;
 b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 95%, 98% and 99% identical to SEQ ID NO: 4 wherein the method comprises:

a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 98% and 99% identical to SEQ ID NO: 4 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is at least 99% identical to SEQ ID NO: 4 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is identical to SEQ ID NO: 4 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a polycyclic musk wherein the receptor is a polypeptide having an amino acid sequence that is identical to SEQ ID NO: 2 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 75% identical to SEQ ID NO: 2 or SEQ ID NO: 4 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 75%, 80%, 85%, 90%, 95%, 98% and 99% identical to SEQ ID NO: 2 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 80%, 85%, 90%, 95%, 98% and 99% identical to SEQ ID NO: 2 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 85%, 90%, 95%, 98% and 99% identical to SEQ ID NO: 2 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 90%, 95%, 98% and 99% identical to SEQ ID NO: 2 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 95%, 98% and 99% identical to SEQ ID NO: 2 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 98% and 99% identical to SEQ ID NO: 2 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 99% identical to SEQ ID NO: 2 wherein the method comprises:
a) contacting the receptor, or a chimera or fragment thereof with a compound;
b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 75%, 80%, 85%, 90%, 95%, 98% and 99% identical to SEQ ID NO: 4 wherein the method comprises:
    a) contacting the receptor, or a chimera or fragment thereof with a compound;
    b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 80%, 85%, 90%, 95%, 98% and 99% identical to SEQ ID NO: 4 wherein the method comprises:
    a) contacting the receptor, or a chimera or fragment thereof with a compound;
    b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 85%, 90%, 95%, 98% and 99% identical to SEQ ID NO: 4 wherein the method comprises:
    a) contacting the receptor, or a chimera or fragment thereof with a compound;
    b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 90%, 95%, 98% and 99% identical to SEQ ID NO: 4 wherein the method comprises:
    a) contacting the receptor, or a chimera or fragment thereof with a compound;
    b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 95%, 98% and 99% identical to SEQ ID NO: 4 wherein the method comprises:
    a) contacting the receptor, or a chimera or fragment thereof with a compound;
    b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 98% and 99% identical to SEQ ID NO: 4 wherein the method comprises:
    a) contacting the receptor, or a chimera or fragment thereof with a compound;
    b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is at least 99% identical to SEQ ID NO: 4 wherein the method comprises:
    a) contacting the receptor, or a chimera or fragment thereof with a compound;
    b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is identical to SEQ ID NO: 4 wherein the method comprises:
    a) contacting the receptor, or a chimera or fragment thereof with a compound;
    b) determining whether the compound has an effect on the activity of the receptor.

Further provided herein is a method for identifying a compound that blocks, inhibits, modulates, and/or enhances the activity of an olfactory receptor that is activated by a nitro musk wherein the receptor is a polypeptide having an amino acid sequence that is identical to SEQ ID NO: 2 wherein the method comprises:
    a) contacting the receptor, or a chimera or fragment thereof with a compound;
    b) determining whether the compound has an effect on the activity of the receptor.

Further provided is any one of a number of musk compounds that activates, mimics, blocks, inhibits, modulates, and/or enhances the activity of an olfactory receptor and that is identified by the methods disclosed herein.

Another embodiment of the invention relates the use of a polypeptide having an amino acid sequence that is at least 75% identical to SEQ ID NO: 2 or SEQ ID NO: 4 for identifying a musk compound that activates, mimics, blocks, inhibits, modulates, and/or enhances the activity of an olfactory receptor.

Still yet further provided is a cell that is recombinantly modified to express a polypeptide described above.

In one embodiment, provided herein is a non-human cell transformed to express a polypeptide having an amino acid sequence that is identical to SEQ ID NO: 2 or SEQ ID NO: 4; more particularly an amino acid sequence that is identical to SEQ ID NO: 2; even more particularly an amino acid sequence that is identical to SEQ ID NO: 4.

Further provided herein is an expression vector comprising a nucleic acid that encodes for a polypeptide having an amino acid sequence that is identical to SEQ ID NO: 2 or SEQ ID NO: 4; more particularly an amino acid sequence that is identical to SEQ ID NO: 2; even more particularly an amino acid sequence that is identical to SEQ ID NO: 4.

In one embodiment provided herein is a cell that is recombinantly modified to express a polypeptide having an amino acid sequence that is at least 75% identical to SEQ ID NO: 2 or SEQ ID NO: 4.

In one embodiment provided herein is a cell that is recombinantly modified to express a polypeptide having an amino acid sequence that is identical to SEQ ID NO: 2 or SEQ ID NO: 4; more particularly an amino acid sequence that is identical to SEQ ID NO: 2; even more particularly an amino acid sequence that is identical to SEQ ID NO: 4.

Further provided herein is a method for identifying a compound that blocks, inhibits, modulates, and/or enhances the activity of an olfactory receptor that is activated by a polycyclic musk wherein the receptor is a polypeptide having an amino acid sequence that is identical to SEQ ID NO: 2 or SEQ ID NO: 4, more particularly an amino acid sequence that is identical to SEQ ID NO: 2; even more particularly an amino acid sequence that is identical to SEQ ID NO: 4. wherein the method comprises:

a) contacting the receptor, or a chimera or fragment thereof with a compound; and
b) determining whether the compound has an effect on the activity of the receptor.

In one embodiment provided herein is a cell wherein the cell is a prokaryotic cell. In another embodiment the cell provided herein is a eukaryotic cell. In a particular embodiment, the cell provided herein is selected from a group consisting of a yeast cell and a plant cell. In a more particular embodiment provided herein the cell is selected from the group consisting of HEK293, CHO, *Xenopus* oocytes, COS, yeast, bacteria and cells derived from the olfactory placode.

In order to identify unknown musk-specific receptors, representative mixtures of musks are used to screen dissociated olfactory sensory neurons (OSNs). Individual musk compounds can be further used for cell-based dose-response experiments performed on specific musk receptors to assess both specificity and sensitivity of the receptors.

For example, Musk compounds are part of a structurally diverse group of chemicals comprising macrocyclic musks, polycyclic musks, alicyclic musks and nitro musks as set forth below.

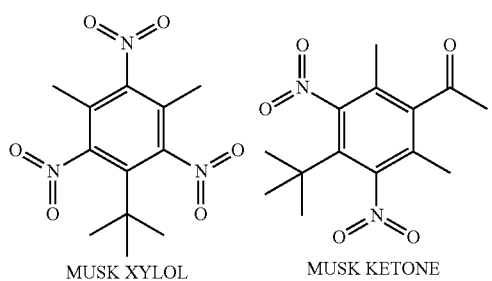

MUSK XYLOL          MUSK KETONE

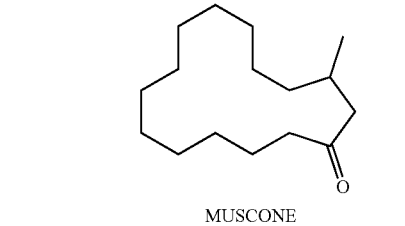

MUSCONE

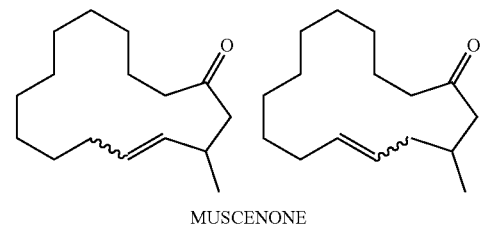

MUSCENONE

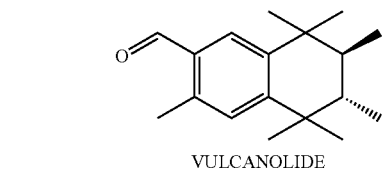

VULCANOLIDE

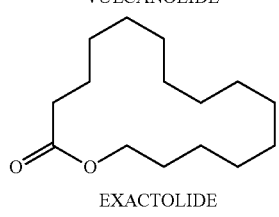

EXACTOLIDE

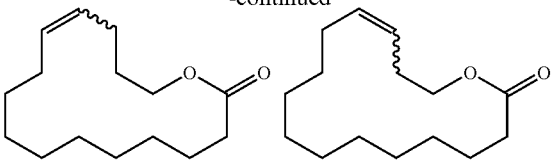

HABANOLIDE

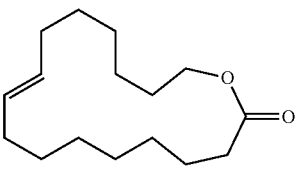

AMBRETTOLIDE

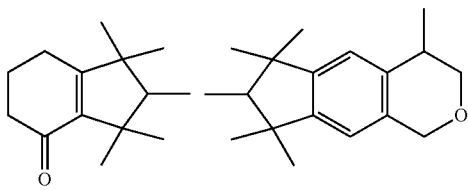

CASHMERAN          GALAXOLIDE

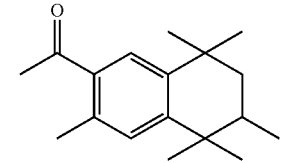

TONALIDE

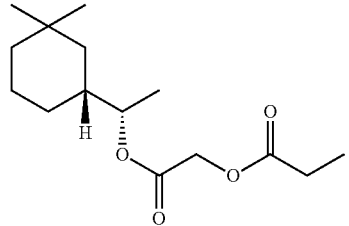

ROMANDOLIDE

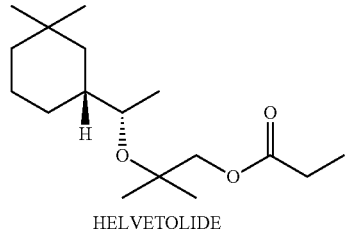

HELVETOLIDE

In one aspect, provided herein are methods to identify mammalian odorant receptors for musk perfume compounds and the use of the receptor for screening, particularly for high throughput screening (HTS) of Musk modulators (e.g. enhancers) and new Musk compounds.

In particular provided herein are mouse receptors, for example Olfr96 (SEQ ID NO: 2) and its human counterpart OR11A1 (SEQ ID NO: 4) as receptors for Musk compounds comprising Vulcanolide, Cashmeran, Tonalide, and Musk X.

While not wishing to be bound to any theory, mouse receptor Olfr235 is a paralog of receptor Olfr1440 and an ortholog of human receptor OR5AN1. These receptors were previously identified as muscone- and muscenone-sensitive receptors (WO2015/020158; Shirasu et al., Neuron (2013)).

In a further embodiment, indicators for monitoring the activity of olfactory receptors are selected from a fluorescent calcium indicator dye, a calcium indicator protein, a fluorescent cAMP indicator, a cAMP response element (CRE) mediated reporter protein, a biochemical cAMP HTRF assay, a beta-arrestin assay, or an electrophysiological recording. Particularly, a calcium indicator dye is selected that can be used to monitor the activity of olfactory receptors expressed on the membrane of the olfactory neurons (e.g., Fura-2 AM).

In a particular embodiment, compounds are screened sequentially and the odorant-dependent changes in calcium dye fluorescence are measured using a fluorescent microscope or fluorescent-activated cell sorter (FACS).

In a further embodiment, molecular 3D receptor modeling of olfactory receptors is used to assess the binding potential in silico and identify compounds that may activate, mimic, block, inhibit, modulate, and/or enhance the activity of an olfactory receptor.

As an example, olfactory neurons are isolated by one or more Musk compounds using either a glass microelectrode attached to a micromanipulator or a FACS machine. Mouse olfactory sensory neurons are screened by $Ca^{2+}$ imaging similar to procedures previously described (Malnic et al., 1999; Areneda et al., 2004; WO2014/210585). Particularly, a motorized movable microscope stage is used to increase the number of cells that can be screened to at least 1,500 per experiment. Since there are approximately 1,200 different olfactory receptors in the mouse and each olfactory sensory neurons expresses only 1 of 1,200 olfactory receptor genes, this screening capacity will cover virtually the entire mouse odorant receptor repertoire. In other words, the combination of calcium imaging for high-throughput olfactory sensory neuron screening leads to the identification of nearly all of the odorant receptors that respond to a particular profile of odorants. In a particular aspect, odorant receptors that respond to Musk compounds can be isolated. For example, at least one neuron is isolated.

For calcium imaging of olfactory neurons, the main olfactory epithelium may be dissected from a mouse before neuronal dissociation. Dissected olfactory epithelium may then be transferred to a dissociation buffer for mechanical and enzymatic dissociation. Dissociated neurons may then be seeded onto a coverslip allowing the screening of thousands of cells by fluorescence microscopy and the cells may be loaded with a calcium sensitive dye (Fura-2 AM) for example for about 30 minutes at 31° C. and transferred onto the microscope ready for screening. Cells are stimulated by perfusing diluted solutions of odorants (in physiological saline) over the dissociated olfactory neurons. The rare cells that respond to the malodor compound are identified by for example stimulating the receptors with 50 μm of the Musk compounds and then by monitoring the intracellular $Ca^{2+}$ flux indicated by changes in Fura-2 fluorescence. After analysis, responding cells may be retrieved from a glass coverslip with a suction micropipette. Isolated cells are then pooled into one sample for subsequent identification of the odorant receptor genes expressed as mRNA in the responding cells.

In a particular embodiment, the mRNA of olfactory neurons are purified and amplified according to the method generally described in Marko, N. F., et al., (2005) A robust method for the amplification of RNA in the sense orientation. BMC genomics, 6, 27; doi:10.1186/1471-2164-6-27 (Eberwine method). At least a portion of the transcriptome (up to including the entire transcriptome) is sequenced using Next-Generation Sequencing (NGS) or hybridized to known genes using Microarray technologies. NGS is generally discussed and described in Metzker, M. L. (2010). Sequencing technologies—the next generation. *Nature reviews. Genetics,* 11(1), 31-46; doi:10.1038/nrg262. In a particular embodiment, a minimum of 5 neurons presenting the same response profile are pooled. The mRNA is released by cell lysis immediately after picking; no DNAse and no purification steps are carried out. The mRNA are amplified by two consecutive rounds of in vitro transcription (IVT). The amplification may be done according to MesageAmpII aRNA kit (Ambion, AMA1751) with the following parameters: two rounds of consecutive 14 hour long IVT.

In a further embodiment, the identity of a group or gene family of Musk olfactory receptors is determined (e.g., up to as many as the number of neurons picked) by comparing the results of the NGS reads obtained from the isolated activated olfactory sensory neurons to a reference genome sequence of the same species. Particularly, the putative Musk receptors will be the most highly abundant mRNA in the olfactory neuron-derived NGS sample or present in more than one independent biological replicate. Because of the combinatorial nature of the olfactory code (one compound activates many ORs and one OR can be activated by many compounds), pooling several neurons activated by given compounds allows the retrieval of virtually all of the receptors responsible for the perception of these molecules in a single NGS experiment. Pooling functionally similar neurons thus greatly improves the deorphanization throughput and speed.

Standard bioinformatics tools are then used to identify the most closely related human odorant receptor(s) to other putative mammalian (non-human) Musk receptor(s) under the assumption that homologous sequence receptors retain similar function. Adipietro et al. (2012) Functional Evolution of Mammalian Odorant Receptors. PLoS Genet 8(7): e1002821. doi:10.1371/journal.pgen.1002821. Default parameters of BLASTP and/or BLASTN algorithm may be used.

The human or non-human mammalian Musk receptors may be adapted to a functional assay that can be used to identify compounds that activate, mimic, block, modulate, and/or enhance the activity of a Musk compound. In particular, the assay may be a cell-based assay or a binding assay and the method for identifying compounds may be a high-throughput screening assay. More particularly, provided herein are receptor-based assays adaptable for high-throughput screening of receptors with compound libraries for the discovery of modulating compounds (e.g., blocking, enhancing and masking).

In a particular embodiment, musk receptor gene sequences are identified from Musk compounds-sensitive cells as follows: Pooled neurons are heated to 75° C. for 10 minutes to break the cell membrane and render their mRNA available for amplification. This amplification step is important when applying NGS technologies with limited amount of starting material, typically between 5 to 15 cells. A linear amplification according to the Eberwine method (IVT) ensures the maintenance of the relative transcription levels of expressed genes. Two consecutive overnight (14h) rounds of in vitro transcription are used to yield sufficient amounts of cRNA; Amplified cRNA is then used to generate an Illumina HiSeq cDNA library. The resulting short sequences of typically 150 base pairs (commonly referred to as "reads") are aligned against the reference genome of the mouse (such as UCSC version mm9 or mm10) in order to build the full transcriptome of these cells. Quantitative analysis of the transcriptome data yields a list of transcribed odorant receptor genes and their respective expression levels. Odorant receptor genes that show the most abundant levels of mRNA (most abundant "reads") or are present in more than one replicate experiment are considered putative Musk compounds receptors.

The predicted mouse OR genes are then used to mine the latest versions of both the mouse and human genome databases in order to identify the most closely related receptors (i.e. highest sequence similarity) in mouse (paralogous genes) and in human (orthologous genes). This process may be performed using the BLAST search algorithm (publically available at the NCBI website), a sequence similarity search tool, where every putative gene sequence previously obtained from the initial transcriptome analysis is used as a query sequence. The newly identified genes identified from this data mining process are also considered as potential Musk receptors under the assumption that paralogous and orthologous genes are highly likely to possess similar activities. In a particular embodiment, pairwise comparison of sequence homology is carried out to identify closely related receptors in mouse and humans using the following iterative scheme:

| Step | Query sequence | BLASTN/BLASTP Result |
|---|---|---|
| 1. | Mouse candidate 1 → | Mouse paralog 1 and human ortholog 1 |
| 2. | Mouse paralog 1 → | Human ortholog 2 |
| 3. | Human ortholog 1 → | Human paralog 2 |
| 4. | Human ortholog 2 → | Human paralog 3 |

Paralog = homolog in same species
Ortholog = homolog in other species

Paralogous genes are then aligned using a multiple alignment tool in order to generate a phylogenetic tree. Functional in vitro data can be interpreted in the light of such a phylogenetic relationship between closely related but distinct receptors. This step is essential in the identification of complete OR gene families that respond, to varying degrees, to the test compounds, for example vulcanolide.

This approach has several major advantages over previously established single cell RT-PCR methods. First, by pooling multiple neurons sharing similar binding properties, a unique mRNA sequencing experiment (NGS) identifies virtually all the receptors that are activated by the target Musk compounds. Therefore the throughput is higher than what was previously achieved. Second, because multiple cells can be pooled into one sample, this approach allows for the selection of genes through a comprehensive comparison of replicate samples across experiments. Third, NGS does not require the use of PCR primers specific to an OR. NGS also does not require the use of degenerate primers specific to ORs, which are problematic and often lead to false positives due to non-linear or non-specific PCR amplification. In particular, since OR coding sequences lie within a single exon, sample contamination with genomic DNA can easily lead to aspecific amplification of OR gene sequences. Fourth, RT-PCR analysis is difficult to perform on pooled samples because of the inherent false positive rate. Single cell mRNA hybridization experiments have been performed using of high-density DNA microarray chips. However, this approach is generally less sensitive than NGS and is further restricted to known genes for which corresponding DNA probes need to be synthesized. Hence, the use of NGS is significantly advantageous to rapidly identify OR and ultimately results in a more accurate selection of candidate receptors compared to the standard (e.g. RT-PCR and microarray) approaches. While the NGS approach is preferred, other approaches may be used such as RT-PCR and microarray approaches.

In a further embodiment, to complete the deorphanization process, the candidate OR genes are further expressed in vitro for confirmation of activity against the compounds used to isolate the olfactory sensory neurons and other structurally-related compounds of interest. The mouse receptors identified from isolated olfactory neurons that respond to both Musk compounds are modified at their N-terminus with short polypeptide sequences (e.g., Flag (SEQ ID NO: 6), Rho (SEQ ID NO: 8; 20 first amino acids of the bovine rhodopsin receptor), or Lucy (SEQ ID NO: 10) tags), transiently expressed in HEK 293T cells, and stimulated separately with Musk compounds to confirm their identity as bona fide Musk compound receptors. Co-expression of the human G alpha subunit $G\alpha_{olf}$ in this cell-based assay activates the Gs transduction pathway that leads to an internal cAMP increase upon binding to the appropriate ligand. Alternatively, co-expression of the human G alpha subunit Gals in the cell based assay activates the Gq transduction pathway that leads to an internal $Ca^{2+}$ increase upon binding to the appropriate ligand. The above process and the results obtained so far serve to validate the process for rapid and reliable identification of mammalian odorant receptors for Musk compounds.

Definitions

The following terms have the meanings ascribed to them unless specified otherwise.

"OR" refers to one or more members of a family of G protein-coupled receptors that are expressed in olfactory cells. Olfactory receptor cells can also be identified on the basis of morphology or by the expression of proteins specifically expressed in olfactory cells. OR family members may have the ability to act as receptors for olfactory transduction.

"OR" nucleic acids encode a family of GPCRs with seven transmembrane regions that have "G protein-coupled receptor activity," e.g., they may bind to G proteins in response to extracellular stimuli and promote production of second messengers such as IP3, cAMP, cGMP, and $Ca^{2+}$ via stimulation of enzymes such as phospholipase C and adenylate cyclase.

The "N terminal domain" region starts at the N-terminus and extends to a region close to the start of the first transmembrane region. "Transmembrane domain," which comprises the seven "transmembrane regions," refers to the domain of OR polypeptides that lies within the plasma membrane, and may also include the corresponding cytoplasmic (intracellular) and extracellular loops. The seven transmembrane regions and extracellular and cytoplasmic loops can be identified using standard methods, as described in Kyte & Doolittle, J. Mol. Biol., 157:105-32 (1982), or in Stryer. The general secondary and tertiary structure of transmembrane domains, in particular the seven transmembrane domains of G protein-coupled receptors such as olfactory receptors, are known in the art. Thus, primary structure sequence can be designed or predicted based on known transmembrane domain sequences, as described in detail below. These transmembrane domains are useful for in vitro ligand-binding assays, both soluble and solid phase.

The phrase "functional effects" in the context of assays for testing compounds that modulate OR family member mediated olfactory transduction includes the determination of any parameter that is indirectly or directly under the influence of the receptor, e.g., functional, physical and chemical effects. It includes ligand binding, changes in ion flux, membrane potential, current flow, transcription, G protein binding, GPCR phosphorylation or dephosphorylation, signal transduction receptor-ligand interactions, second messenger concentrations (e.g., cAMP, cGMP IP3, or intracellular $Ca.^{2+}$), in vitro, in vivo, and ex vivo and also includes other physiologic effects such increases or decreases of neurotransmitter or hormone release.

By "determining the functional effect" or "confirming the activity" in the context of assays is meant assays for a compound that increases or decreases a parameter that is indirectly or directly under the influence of an OR family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte OR gene expression; tissue culture cell OR expression; transcriptional activation of OR genes; ligand-binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," "counteractants" and "modulators" of OR genes or proteins are used interchangeably to refer to inhibitory, activating, or modulating molecules identified using in vivo, in vitro and in vivo assays for olfactory transduction, e.g., ligands, agonists, antagonists, enhancers, and their homologs and mimetics. Inhibitors are compounds that, e.g., bind to, partially or totally block stimulation, decrease, prevent, delay activation, inactivate, desensitize, or down regulate olfactory transduction, e.g., antagonists. Activators are compounds that, e.g., bind to, stimulate, increase, open activate, facilitate, enhance activation, sensitize, or up regulate olfactory transduction, e.g., agonists. Modulators include compounds that, e.g., alter the interaction of a receptor with: extracellular proteins that bind activators or inhibitor (e.g., odorant-binding proteins, ebnerin and other members of the hydrophobic carrier family); G proteins; kinases (e.g., homologs of rhodopsin kinase and beta adrenergic receptor kinases that are involved in deactivation and desensitization of a receptor); and arrestins, which also deactivate and desensitize receptors. Modulators can include genetically modified versions of OR family members, e.g., with altered activity, as well as naturally occurring and synthetic ligands, antagonists, agonists, small chemical molecules and the like. Such assays for inhibitors and activators include, e.g., expressing OR family members in cells or cell membranes, applying putative modulator compounds, in the presence or absence of flavor or fragrance molecules, e.g. Musks, and then determining the functional effects on olfactory transduction, as described above. Samples or assays comprising OR family members that are treated with a potential activator, inhibitor, or modulator are compared to control samples without the inhibitor, activator, or modulator to examine the extent of modulation. Control samples (untreated with modulators) are assigned a relative OR activity value of 100%. Inhibition of an OR is achieved when the OR activity value relative to the control is about 80%, optionally 50% or 25-0%. Activation of an OR is achieved when the OR activity value relative to the control is 110%, optionally 150%, optionally 200-500%, or 1000-3000% higher.

The terms "purified," "substantially purified," and "isolated" as used herein refer to the state of being free of other, dissimilar compounds with which the compound of the invention is normally associated in its natural state, so that the "purified," "substantially purified," and "isolated" subject comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample. As used herein, the terms "purified," "substantially purified," and "isolated" "isolated," when referring to a nucleic acid or protein, of nucleic acids or proteins, also refers to a state of purification or concentration different than that which occurs naturally in the mammalian, especially human, body. Any degree of purification or concentration greater than that which occurs naturally in the mammalian, especially human, body, including (1) the purification from other associated structures or compounds or (2) the association with structures or compounds to which it is not normally associated in the mammalian, especially human, body, are within the meaning of "isolated." The nucleic acid or protein or classes of nucleic acids or proteins, described herein, may be isolated, or otherwise associated with structures or compounds to which they are not normally associated in nature, according to a variety of methods and processes known to those of skill in the art.

As used herein, the term "isolated," when referring to a nucleic acid or polypeptide refers to a state of purification or concentration different than that which occurs naturally in the mammalian, especially human, body. Any degree of purification or concentration greater than that which occurs naturally in the body, including (1) the purification from other naturally-occurring associated structures or compounds, or (2) the association with structures or compounds to which it is not normally associated in the body are within the meaning of "isolated" as used herein The nucleic acids or polypeptides described herein may be isolated or otherwise associated with structures or compounds to which they are not normally associated in nature, according to a variety of methods and processed known to those of skill in the art.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs) for amplifying (e.g., by polymerase chain reaction, PCR) naturally expressed (e.g., genomic DNA or mRNA) or recombinant (e.g., cDNA) nucleic acids of the invention in vivo or in vitro.

The term "7-transmembrane receptor" means a polypeptide belonging to a superfamily of transmembrane proteins that have seven domains that span the plasma membrane seven times (thus, the seven domains are called "transmembrane" or "TM" domains TM I to TM VII). The families of olfactory and certain taste receptors each belong to this super-family. 7-transmembrane receptor polypeptides have similar and characteristic primary, secondary and tertiary structures, as discussed in further detail below.

The term "nucleic acid" or "nucleic acid sequence" refers to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating, e.g., sequences in which the third position of one or more selected codons is substituted with mixed-base and/or deoxyinosine residues.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" means also the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention. "Recombinant" means also modifications obtained by genome editing techniques, such as CRISPR/Cas9, of a cell that leads to stable or transient expression of endogenous genes such as the receptor gene referred to herein.

The term "expression vector" refers to any recombinant expression system for the purpose of expressing a nucleic acid sequence of the invention in vitro or in vivo, constitutively or inducibly, in any cell, including prokaryotic, yeast, fungal, plan insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression "cassettes which contain only the minimum elements needed for transcription of the recombinant nucleic acid.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa, HEK-293, and the like, e.g., cultured cells, explants, and cells in vivo.

Nucleic acid and amino acid sequences identified and/or used herein are listed below:

```
Mouse Olfr96 (SEQ ID NO: 1 DNA; SEQ ID NO: 2 PROTEIN)
                                                    SEQ ID NO: 1
atgggaatcctttccacaggaaatcaaactgtcactgagtttgtacttcttggtttccatgaagtccctgggctg cacctcctgttttttctgtgttcaccatcctctatgcctccatcatcacagggaacatgctcattgcagtggtg gtggtgagctcccagaggcttcacacacccatgtatttctttctggtgaatctgtccttcatagagattgtctat acctccacagtggtgcccaaaatgctggaaggcttcttacaggaggccaccatatctgtggctggctgcttgctc cagttctttgttttggctctctggccacagatgagtgttttctgctggctgtgatggcatatgatcgatatctc gcaatttgtcaccctctacgatacccacacctcatgggcctcaatggtgcctggggttggtgctcacagtctgg ctgtctggcttcatggtagatggactagttgttgctctgatggcccagttgagattctgtggcccaacttagtt gatcacttttactgtgattttcaccttgatggtcctggcttgctcagatacccaagtggcccaggtgactaca tttgttctctctgtggtcttcctgactgtccctttgggctggttctgatctcctatgctcagattgtagtgact gtgctgagagttccttctgggaccagaagaaccaaggccttctccacatgctcctctcacctggctgtggtgtcc acgttctatggaacactcatggtattgtacattgtgccctctgctgttcattctcagctcctctccaaggtcatt gccctgctctacacagtggtcactcccatcttcaaccctgtcatctacaccttgaggaaccaggaggtgcagcag gcactaagaaggcttctctactgcaaaccaactgaaatgtga
```

SEQ ID NO: 2
MGILSTGNQTYTEFYLLGFHEVPGLHLLFFSVFTILYASIITGNMLIAVVVSSQRLHTPMYFFLVNLSFIEIVY
TSTVVPKMLEGFLQEATISVAGCLLQFFVFGSLATDECFLLAVMAYDRYLAICHPLRYPHLMGPQWCLGLYLTVW
LSGFMVDGLVVALMAQLRFCGPNLVDHFYCDFSPLMVLACSDTQVAQVTTFVLSVVFLTYPFGLVLISYAQIVVT
VLRVPSGTRRTKAFSTCSSHLAVVSTFYGTLMVLYIVPSAVHSQLLSKVIALLYTVVTPIFNPVIYTLRNQEVQQ
ALRRLLYCKPTEM

Human OR11A1 (SEQ ID NO: 3 DNA; SEQ ID NO: 4 PROTEIN)

SEQ ID NO: 3
atggaaattgtctccacaggaaacgaaactattactgaatttgtcctccttggcttctatgacatccctgaactg
catttcttgttttttattgtattcactgctgtctatgtcttcatcatcatagggaatatgctgattattgtagca
gtggttagctcccagaggctccacaaacccatgtatattttcttggcgaatctgtccttcctggatattctctac
acctccgcagtgatgccaaaaatgctggagggcttcctgcaagaagcaactatctctgtggctgttgcttgctc
cagttctttatcttcggctctctagccacagctgaatgcttactgctggctgtcatggcatatgaccgctacctg
gcaatttgctacccactccactacccactcctgatggggcccagacggtacatggggctggtggtcacaacctgg
ctctctggatttgtggtagatggactggttgtggccctggtggcccagctgaggttctgtggccccaaccacatt
gaccagttttactgtgactttatgcttttcgtgggcctggcttgctcggatcccagagtggctcaggtgacaact
ctcattctgtctgtgttctgcctcactattccttttggactgattctgacatcttatgccagaattgtggtggca
gtgctgagagttcctgctggggcaagcaggagaagggctttctccacatgctcctcccacctagctgtagtgacc
acattctatggaacgctcatgatcttttatgttgcaccctctgctgtccattcccagctcctctccaaggtcttc
tccctgctctacactgtggtcacccctctcttcaatcctgtgatctataccatgaggaacaaggaggtgcatcag
gcacttcggaagattctctgtatcaaacaaactgaaacacttgattga SEQ ID NO: 4
MEIVSTGNETITEFVLLGFYDIPELHFLFFIVFTAVYVFIIIGNMLIIVAVVSSQRLHKPMYIFLANLSFLDILY
TSAVMPKMLEGFLQEATISVAGCLLQFFIFGSLATAECLLLAVMAYDRYLAICYPLHYPLLMGPRRYMGLVVTTW
LSGFVVDGLVVALVAQLRFCGPNHIDQFYCDFMLFVGLACSDPRVAQVTTLILSVFCLTIPFGLILTSYARIVVA
VLRVPAGASRRRAFSTCSSHLAVVTTFYGTLMIFYVAPSAVHSQLLSKVFSLLYTVVTPLFNPVIYTMRNKEVHQ
ALRKILCIKQTETLD Flag tag (SEQ ID NO: 5 DNA; SEQ ID NO: 6 PROTEIN)

SEQ ID NO: 5
gattacaaggacgacgacgataag

SEQ ID NO: 6
DYKDDDDK

Rho tag (SEQ ID NO: 7 DNA; SEQ ID NO: 8 PROTEIN)

SEQ ID NO: 7
atgaacgggaccgagggcccaaacttctacgtgcctttctccaacaagacgggcgtggtg

SEQ ID NO: 8
MNGTEGPNFYVPFSNKTGVV

Lucy tag (SEQ ID NO: 9 DNA; SEQ ID NO: 10 PROTEIN)

SEQ ID NO: 9
atgagaccccagatcctgctgctcctggccctgctgaccctaggcctggct

SEQ ID NO: 10
MRPQILLLLALLTLGLA

The following examples are illustrative only and are not meant to limit the scope of invention as set forth in the Summary, Description or in the Claims.

EXAMPLES

Example 1

The Identification of Polycyclic Musk Receptors Mouse Olfr96 and Human OR11A1

Musk responsive cells were isolated and further processed for Next Generation Sequencing (NGS) based transcriptome analysis. A mixture of Cashmeran, Tonalide and Galaxolide was prepared (Mix A). A mixture of Muscone, Muscenone and Habanolide was also prepared (Mix B). Each individual Musk was blended at a final concentration of 50 µM. $Ca^{2+}$ imaging traces were recorded for distinct Olfactory Sensory Neurons (OSNs) that were activated by mix A and/or mix B. The Y axis of FIG. 1A shows the average intensity of the relative fluorescent unit as a result of a ratiometric 340/380 nm $Ca^{2+}$ imaging recording. The X axis of FIG. 1A shows the time frames (8s/frame). Responding cells were pooled for RNA extraction and subsequent Next-Generation-Sequencing experiment (i.e. RNAseq). All expression levels were further normalized to olfactory marker protein (OMP). The analysis of the resulting transcriptome analysis revealed the most highly expressed odorant receptors (i.e. most abundant read counts, normalized by FPKM): Olfr235 and Olfr96 (FIG. 1B). They correspond to the following human orthologous genes: OR5AN1 and OR11A1, respectively.

Example 2

Figure 2:
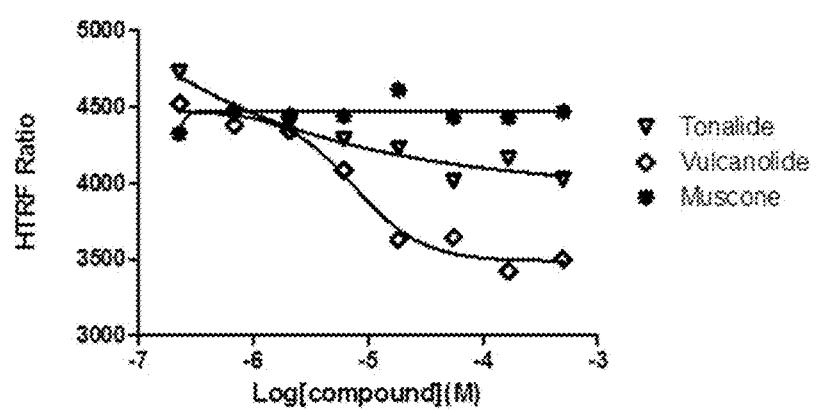
FIG. 2 shows Musk dose response curves of Olfr96 with polycyclic musk compounds vulcanolide and tonalide.
Figure 3:
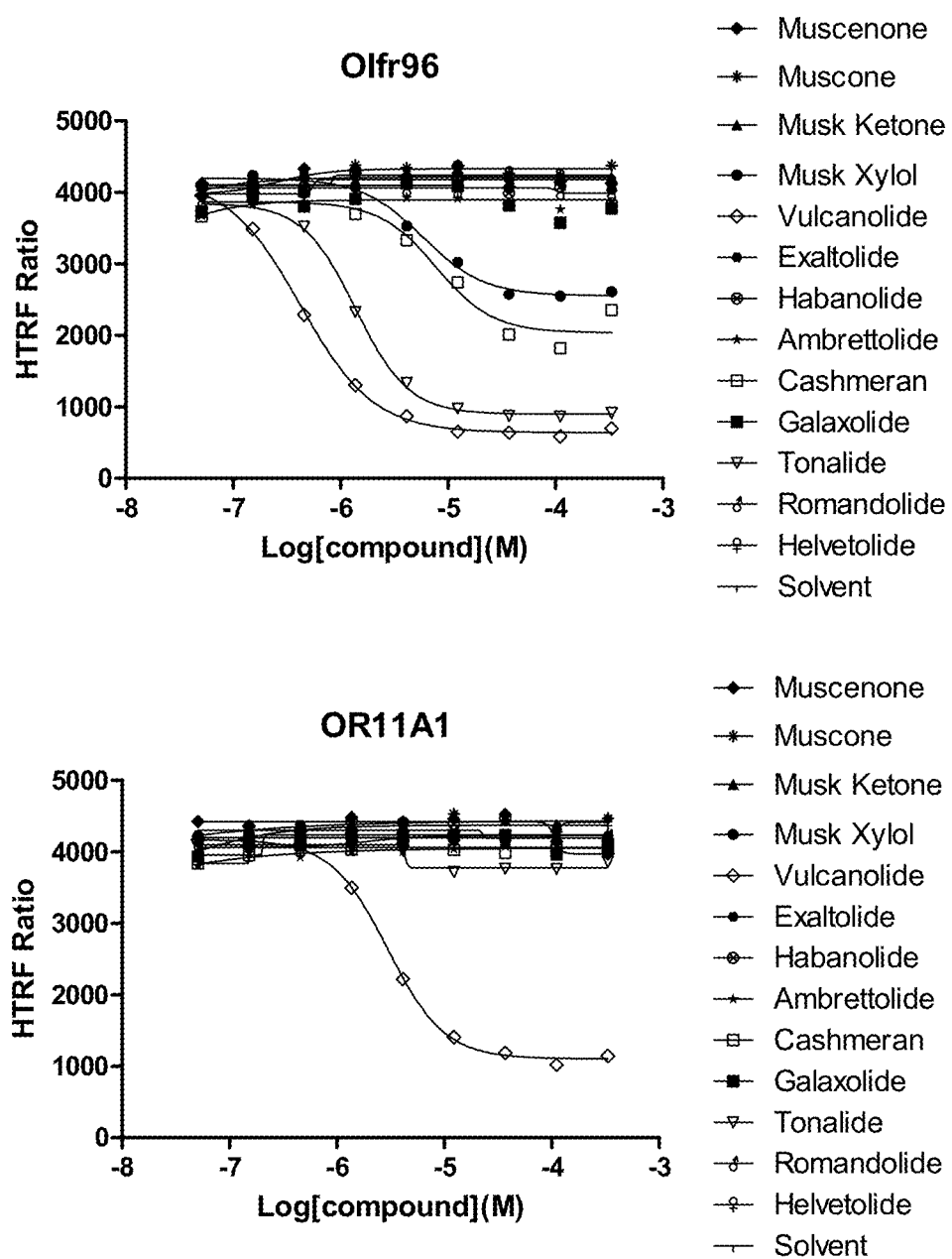
FIG. 3 shows Musk dose response curves of Olfr96 and OR11A1 with polycyclic musk compounds vulcanolide, tonalide and cashmeran, and nitro musk compound Musk X.

Functional Characterization of Mouse Olfr96 and Human OR11A1 Musk Receptors Functional dose-response experiments were performed to evaluate the level of functional activity of the modified cell line. Using a cell-based assay, mouse Olfr96 was tested in an HEK293T cell line wherein the endogenous RTP1 gene has been activated and the odorant receptor chaperone was expressed. Flag-Rho-tagged receptor genes were co-transfected with the olfactory canonical G-protein Golf gene and were exposed to increasing concentrations of the Musk odorants Tonalide, Vulcanolide, and Muscone. Odorant-induced activity was detected by measuring the cAMP increase in the cytosol using an HTRF based kit (CisBio, cAMP dynamic 2 kit, 62AM4PEJ). A dose-dependent increase of Olfr96 receptor activity is observed for the 2 polycyclic Musks (Tonalide and Vulcanolide), but not the macrocyclic Musk, Muscone (FIG. 2). In an additional repeat experiment using the same conditions, mouse Olfr96 and corresponding human ortholog OR11A1 were tested side by side in duplicate with a musk diversity set for specificity assessment. Lucy-Flag-Rho-tagged receptor genes were co-transfected with the olfactory canonical G-protein Golf gene and were exposed to increasing concentrations of the macrocyclic Musk odorants Muscenone, Muscone, Habanolide and Exaltolide; the polycyclic Musk odorants Tonalide, Vulcanolide, Cashmeran, Galaxolide; the alicyclic Musk odorants Helvetolide, Ambretolide and Romandolide; and the nitro Musk odorants Musk C and Musk X. A dose-dependent increase of Olfr96 receptor activity is observed for 3 polycyclic Musks (Tonalide, Cashmeran and Vulcanolide) and a nitro Musk (Musk X), but not Musk C, Galaxolide, the macrocyclic Musks or the alicyclic Musks (FIG. 3); and a dose-dependent increase of OR11A1 receptor activity is observed for 1 polycyclic Musks (Vulcanolide), but not the macrocyclic Musks, the alicyclic Musks or the nitro Musk or the other polycyclic Musks (FIG. 3).

Example 3

Identification of Compounds that Enhance the Activation of Musk Receptors

A musk receptor is exposed to a binary mixture of a known musk compound and a compound to be evaluated. Any enhancement of the "Musk" receptor activity provided by the compound is measured. This is done by performing Musk dose response measurement in the presence and in the absence of specific compounds that enhance the activity of the receptor. The same cell-based assay is used as in example 2. If the compound enhances the receptor activity, then the concentration of Musk compound needed to attain the equivalent level of receptor activation in the absence of the compound is reduced. Typically this is done with a dose response experiment and is illustrated with a dose response curve that is for example displayed or indicated by a leftward shift in the curve and reduction in the calculated EC50 value.

What is claimed is:

1. A method for identifying a compound that activates, mimics, blocks, inhibits, modulates, and/or enhances the activity of an olfactory receptor that is activated by a polycyclic musk compound and/or by musk X, wherein the receptor is a polypeptide having an amino acid sequence represented by SEQ ID NO: 2 or SEQ ID NO: 4, wherein the method comprises:
   a) contacting the receptor or a cell that is recombinantly modified to express a polypeptide, wherein the cell comprises
      i) a nucleic acid encoding the polypeptide which comprises an amino acid sequence that is identical to SEQ ID NO: 2 or to SEQ ID NO: 4; or
      ii) an expression vector comprising a nucleic acid that encodes for a polypeptide comprising an amino acid sequence that is identical to SEQ ID NO: 2 or SEQ ID NO: 4; or a nucleic acid that comprises a nucleotide sequence that is identical to SEQ ID NO: 1 or SEQ ID NO: 3;
   with a compound in the presence of the polycyclic musk compound and/or the musk X; and
   b) detecting whether the compound has an effect on the activity of the receptor.

2. The method as recited in claim 1, wherein the polycyclic compound is selected from the group consisting of a tonalide, vulcanolide, and cashmeran.

* * * * *